United States Patent [19]

Kadokura et al.

[11] Patent Number: 5,066,530
[45] Date of Patent: Nov. 19, 1991

[54] LAMINA AND A COSMETIC COMPRISING THE SAME

[75] Inventors: Hidekimi Kadokura; Kunio Saegusa, both of Niihama, Japan

[73] Assignee: Sumitomo Chemical Company, Limited, Osaka, Japan

[21] Appl. No.: 412,129

[22] Filed: Sep. 25, 1989

Related U.S. Application Data

[62] Division of Ser. No. 119,092, Nov. 10, 1987, Pat. No. 4,882,143.

[30] Foreign Application Priority Data

Nov. 17, 1986 [JP] Japan .................................. 61-273396

[51] Int. Cl.$^5$ .............................................. B32B 3/00
[52] U.S. Cl. ...................................... 428/98; 428/323; 428/328; 428/212; 428/688; 428/698
[58] Field of Search .................. 428/98, 323, 328, 212, 428/688, 698

[56] References Cited

U.S. PATENT DOCUMENTS

| | | | |
|---|---|---|---|
| 3,018,186 | 1/1962 | Jenkins | 106/253 |
| 3,449,487 | 6/1969 | Micco et al. | 264/140 |
| 4,438,094 | 3/1984 | Oppenlaender et al. | 424/69 X |
| 4,534,963 | 8/1985 | Gordon | 424/69 |
| 4,710,373 | 12/1987 | Nakamura et al. | 414/69 X |
| 4,923,908 | 5/1990 | Lostumo et al. | 523/220 |

FOREIGN PATENT DOCUMENTS

| | | |
|---|---|---|
| 0268938 | 1/1988 | European Pat. Off. . |
| 57-109712 | 7/1982 | Japan .................................. 424/69 |
| 2007480 | 5/1979 | United Kingdom . |

Primary Examiner—Patrick J. Ryan
Attorney, Agent, or Firm—Stevens, Davis, Miller & Mosher

[57] ABSTRACT

A lamina having an excellent capacity of scattering ultraviolet rays comprising a laminar substance as a matrix and a finely divided metal or metal compound dispersed therein, wherein the difference in refractive index between the laminar substance and the finely divided metal or metal compound is not less than 0.1, and a cosmetic comprising the same as a UV screener.

15 Claims, 3 Drawing Sheets

LAMINA AND A COSMETIC COMPRISING THE SAME

This is a division of application Ser. No. 07/119,092, filed Nov. 10, 1987, now U.S. Pat. No. 4,882,143.

The present invention relates to a lamina having an excellent capacity of scattering ultraviolet rays comprising a laminar substance as a matrix and a finely divided metal or metal compound dispersed therein and to a cosmetic comprising the same as a UV screener.

UV screeners are for screening ultraviolet rays by scattering or absorbing ultraviolet rays. For this purpose, organic compounds have been used such as salycilic acid, p-aminobenzoic acid, cinnamic acid, esters thereof and benzophenones and powder of metal oxides such as titania, zinc oxide, iron oxide and the like. It has also been known that the UV screening ability of the powder of metal oxides reaches a maximum when the ratio of the diameter of the powder to the wavelength of rays is $\frac{1}{2}$.

The powder of metal oxides is also used as oxidation catalysts. The known methods for preparing the same include (1) a method comprising adding aqueous ammonia or urea to metal chloride or metal sulfate to hydrolyze the same and calcining the resulting hydroxide and (2) a method comprising mixing $TiO_2 \cdot nH_2O$ and $Zn(OH)_2$ obtained by hydrolysis of titanium isopropoxide and zinc nitrate, respectively, and calcining the mixture ["Catalyst", Vol. 19, No. 5, pp. 350-2, published by Catalysis Society of Japan].

A method has also been known which comprises hydrolyzing a mixture of a silicon alkoxide and a titanium alkoxide and calcining the resulting hydrolysate, and it has also been known to use the resulting product as an additive for a cosmetic having a UV screening ability [Japanese Patent Application Kokai (Laid-Open) No. 227,813/84].

In addition, there has been known a method for preparing finely divided particles by oxidatively decomposing or hydrolyzing the sublimate of titanium chloride with oxygen or steam, respectively. The finely divided particles thus obtained have a particle diameter of about 0.002–0.05 μm.

Zinc oxide can be prepared by the vapor phase oxidation of vapor of metallic zinc, and the finely divided particles thus obtained have a particle diameter of about 0.05–0.5 μm.

The powder of zinc oxide, iron oxide or titania obtained according to such methods has an excellent UV screening ability when it is in the form of finely divided particles. However, such a powder has a problem that the finely divided particles tend to agglomerate, so that when they are incorporated with cosmetics, paints and the like, the latter are inferior in spreading property and poor in feel when used.

Since these finely divided metal oxides have a large surface area and a high surface activity, they have a catalytic activity for oxidation and, in some applications, cause coexisting organic substances to deteriorate.

Under such circumstances, the present inventors have made extensive research on UV screeners having not only an excellent capacity of scattering ultraviolet rays, but also an excellent dispersibility in a medium giving cosmetics and the like a good feeling in use by incorporating the screeners thereinto and causing no deterioration of coexisting organic substances in cosmetics and the like.

It is an object of this invention to provide a lamina having an excellent capacity of scattering ultraviolet rays.

It is another object to provide a lamina having a good dispersibility in cosmetics, paints and the like.

It is still another object to provide cosmetics having incorporated thereinto the lamina and a good feeling in use in respect of spreading property and the like.

Other objects and advantages of this invention will become apparent from the following description.

According to this invention, there is provided a lamina comprising a laminar substance as a matrix and a finely divided metal or metal compound dispersed therein, wherein the difference in refractive index between the laminar substance and the finely divided metal or metal compound is not less than 0.1.

This invention also provides a cosmetic comprising the above lamina.

The lamina of the present invention is superior in ability to screen ultraviolet rays, especially those having a wavelength of not more than 400 nm, and dispersability in resins or vehicles compared with conventional metal oxide powders. Therefore, when the lamina is incorporated into cosmetics, paints, films for agriculture and the like, a good feel is given in use of them in respect of spreading property. Moreover, the lamina causes no deterioration of coexisting organic substances. Hence, the lamina of the present invention can be used as a UV screener not only in cosmetic but also in paints, films for agriculture and the like, and has a very great industrial value.

In the accompanying drawings.

The laminar substance used as a matrix in the lamina of the present invention includes bivalent or higher polyvalent metals; oxides, nitrides, carbides and hydroxides of the metals; hydrolysates of metal chlorides; partial hydrolysates of organometallic compounds such as metal alkoxides, metal chelate compounds and metal salts of organic acids; inorganic and organic compounds of a high molecular weight; and the like.

Specifically, the metals include magnesium, zinc, aluminum, indium, silicon, tin, titanium, zirconium, chromium, molybdenum, tungsten, iron, cobalt and nickel and the like; the oxides, nitrides, carbides and hydroxides of metals include those of these metals; the metal chlorides include partial hydrolysates of silicon tetrachloride, titanium tetrachloride, zirconium tetrachloride and the like; the partial hydrolysates of metal alkoxides include partial hydrolysates of magnesium diethoxide, magnesium diisopropoxide, zinc diethoxide, zinc diisopropoxide, aluminum triisopropoxide, aluminum tributoxide, indium triethoxide, indium trioctoxide, tetraethoxy silane, tetrabutoxy silane, tin tetraethoxide, tin tetraoctoxide, titanium tetraethoxide, titanium tetraisopropoxide, zirconium tetraethoxide, zirconium tetrapentoxide, chromium uriethoxide, chromium tributoxide, molybdenum hexaethoxide, molybdenum hexabutoxide, tungsten hexaisopropoxide, iron diisopropoxide, iron tributoxide, cobalt dibutoxide, cobalt diisopropoxide, nickel diisopropoxide, nickel dibutoxide and the like; the partial hydrolysates of metal chelate compounds include acetyl acetonates of magnesium, zinc, aluminum, indium, silicon, tin, titanium, zirconium, chromium, molybdenum, tungsten, iron, cobalt, nickel and the like; the partial hydrolysates of organic acids include aluminum acetate, indium formate, silicon acetate, tin acetate, titanium formate, titanium acetate, zirconium propionate and the like; the inorganic compounds of a high molecular weight include water glass, aluminum phosphate solution, zirconium phosphate, phosphazenes and the like; the organic compounds of a high molecular weight include polyethylene, polypropylene, polystyrene, polyesters, polymethyl methacrylate, polyvinyl chloride, ethyl cellulose, methyl cellulose, nitrocellulose, polyvinyl alcohol, polyimides, epoxy resins, phenol resins and the like.

The finely divided metal or metal compound dispersed in the laminar substance includes bivalent or higher polyvalent metals; oxides, nitrides, carbides and hydroxides of the metals; hydrolysates of metal chlorides; partial hydrolysates of organometallic compounds such as metal alkoxides, metal chelate compounds, metal salts of organic acids and the like; metal sulfates; and the like. Preferred are bivalent or higher polyvalent metals and oxides, nitrides, carbides and hydroxides of the metals. Oxides of the metals are more preferable.

Specifically, the metals include magnesium, zinc, aluminum, indium, silicon, tin, titanium, zirconium, chromium, molybdenum, tungsten, iron, cobalt, nickel and the like; the oxides, nitrides, carbides and hydroxides of the metals include oxides, nitrides, carbides and hydroxides of these metals; the hydrolysates of metal chlorides include silicon tetrachloride, titanium tetrachloride, zirconium tetrachloride and like; the partial hydrolysates of metal alkoxides includes partial hydrolysates of magnesium diethoxide, magnesium diisopropoxide, zinc diethoxide, zinc diisopropoxide, aluminum triisopropoxide, aluminum triisobutoxide, indium triethoxide, indium trioctoxide, tetraethoxy silane, tetrabutoxy silane, tin tetraethoxide, tin tetraoctoxide, titanium tetraethoxide, titanium tetraisopropoxide, zirconium tetraethoxide, zirconium tetrapentoxide, chromium triethoxide, chromium tributoxide, molybdenum hexaethoxide, molybdenum hexabutoxide, tungsten hexaisopropoxide, iron diisopropoxide, iron tributoxide, cobalt dibutoxide, cobalt diisopropoxide, nickel diisopropoxide, nickel dibutoxide and the like; the partial hydrolysates of metal chelate compounds include partial hydrolysates of acetylacetonate of magnesium, zinc, aluminum, indium, silicon, tin, titanium, zirconium, chromium, molybdenum, tungsten, iron, cobalt, nickel and the like; the partial hydrolysates of metal carboxylates include partial hydrolysates of aluminum acetate, indium formate, silicon acetate, tin acetate, titanium formate, titanium acetate, zirconium propionate and the like.

As the finely divided metal or metal compound, the following may preferably be used: commercially available metallic fine powders of nickel, silver, copper, aluminum, gold, iron and the like (for example, those mfd. by Shinkuu Yakin Co., Ltd. or Mitsui Mining & Smelting Co., Ltd.); finely divided particles of iron oxide, silica, alumina and titania (for example, those mfd. by Okamura Seiyu Co., Ltd., Nippon Aerosil Co., Ltd. or Sumitomo Chemical Co., Ltd.); finely divided particles of silicon carbide (for example, those mfd. by Showa Denko K.K.) and finely divided particles of silicon nitride (for example, those mfd. by Ube Industries, Ltd.).

The metal hydroxides may be magnesium hydroxide, barium hydroxide, iron hydroxide, aluminum hydroxide and the like which are easily obtained by a known procedure such as addition of an alkali to an aqueous solution of a corresponding metal salt.

The metal sulfate can be obtained by neutralization of an aqueous solution of a corresponding metal hydroxide or salt with sulfuric acid. It may be, for example, superfinely divided barium sulfate obtained by the reaction of an aqueous solution of barium hydroxide with sulfuric acid.

Partial hydrolysates of the above-mentioned metal alkoxides or modification products of said metal alkoxides with organic acids can also be used as the finely divided metal compound in the present invention. For example, finely divided particles of monodisperse can be obtained by adding a proper amount of water and ammonia to an ethanol solution of tetraethoxy silane. Finely divided particles can also be obtained by blowing into the air an alcoholic solution containing aluminum propoxide and a proper amount of stearic acid from a nozzle or the like.

The average particle diameter of the finely divided metal or metal compound used in the present invention is preferably about 0.005–0.5 $\mu$m, more preferably about 0.008–0.1 $\mu$m. When the average particle diameter is larger than 0.5 $\mu$m, it tends to be difficult to uniformly disperse the metal or metal compound in the laminar substance. And the capacity of scattering ultraviolet rays tends to be reduced since the average particle diameter becomes larger than the wavelength. On the other hand, when the average particle diameter is smaller than 0.005 $\mu$m, the difference in particle size between the finely divided particles and the matrix tends to be insignificant.

Any known method can be utilized for adding the finely divided metal or metal compound to, mixing the same with and dispersing the same in the laminar substance as the matrix as far as it can uniformly disperse the finely divided metal or metal compound in the laminar substance. A laminar substance comprising a metal oxide as the matrix can be obtained by the following method described in U.S. Pat. No. 2,941,895 or Japanese Patent Application No. 176,906/85. Combining the above-mentioned methods, we can obtain a laminar comprising a metal oxide as a matrix and a finely divided metal or metal compound dispersed therein: After dispersing a finely divided metal or metal compound in a metal alkoxide solution, the dispersion is coated onto a smooth-surface of a substrate. Thereafter, the resulting coating film is subjected to hydrolysis with water or steam to obtain a lamina in which a finely divided metal or metal compound dispersed in a partial hydrolysate of the metal alkoxide as a matrix, and the lamina is exfoliated by a scraper or the like and then calcined in the air. When the calcination is effected in a reductive atmosphere such as in the presence of carbon or the like, there is obtained a lamina comprising a matrix composed mainly of metal carbide and a finely divided metal or metal compound dispersed therein. Alternatively, when the calcination is effected in a nitrogen atmosphere in the presence of carbon, there is obtained a lamina comprising a matrix composed mainly of metal nitride and a finely divided metal or metal compound dispersed therein.

A lamina comprising titania as the matrix and a finely divided metal or metal compound dispersed therein can be obtained by dispersing a finely divided metal or metal compound in an aqueous solution of titanium sulfate and making a laminar substance by the method described in U.S. Pat. No. 3,018,186.

Moreover, a lamina comprising titanium carbide or titanium nitride as the matrix and a finely divided metal or metal compound can be obtained by changing the atmosphere in the calcination in the above-mentioned method.

Similarly, various laminae comprising as the matrix an organic compound of a high molecular weight such as polyethylene, polypropylene, polystyrene, a polyester, polymethyl methacrylate, polyvinyl chloride, ethyl cellulose, methyl cellulose, nitrocellulose, polyvinyl alcohol, a polyimide or the like and a finely divided metal or metal compound dispersed therein can be obtained by kneading the finely divided metal or metal compound with the organic compound by means of a roll mill or the like or by laminating a dispersion of the finely divided metal or metal compound in a solvent solution of the above-mentioned organic compound by means of a known drum flaker or by the method disclosed in Japanese Patent Application No. 82,486/86.

Also, according to the method described in Japanese Patent Application No. 82,486/86, a dispersion of the finely divided metal or metal compound in a solution of an inorganic compound of a high molecular weight such as water glass or aluminum phosphate solution can be laminated.

In such cases, the resulting lamina may be calcined in order to improve the stability in the air.

When the matrix is a metal oxide, a metal nitride, a partial hydrolysate of a metal alkoxide or a metal carbide, the above-mentioned method comprising dispersing the finely divided metal or metal compound in a metal alkoxide solution and then hydrolyzing the metal alkoxide is most preferred in view of uniform quality and productivity.

Since there is a distribution in size and thickness of the lamina, the size and thickness are indicated by average size and thickness which are defined as the mean values of the respective values "(maximum length of lamina +minimum length of lamina)/2" and "(maximum thickness of lamina +minimum thickness)/2" of 100 laminae.

Average thickness and size of the lamina of the present invention are not critical. However, the average size of the lamina is preferably about 1–500 $\mu$m, more preferably 3–100 $\mu$m. When the average size of the lamina is less than about 1 $\mu$m, it becomes difficult to maintain the form of a lamina. On the other hand, when the average size of the lamina is more than 500 $\mu$m, the lamina becomes easy to break.

The average thickness of the lamina is preferably about 0.1–5 $\mu$m, more preferably 0.2–2 $\mu$m. When the average thickness is less than about 0.1 $\mu$m, the mechanical strength of the lamina tends to become so weak that the lamina cannot be used in practice. On the other hand, when the average thickness of the lamina is more than about 5 $\mu$m, the adhesiveness to skin and feel in use of cosmetics comprising the lamina tend to be inferior.

The aspect ratio of the lamina defined as follows is not critical though it is preferably 3–100:

$$\text{Aspect Ratio} = \frac{\text{Average Size of the Lamina}}{\text{Average Thickness of the Lamina}}$$

When the aspect ratio is less than 3, the spreading property of the cosmetics comprising the lamina tends to become low. On the other hand, when the aspect ratio is more than 100, the lamina tends to be broken mechanically.

In order to obtain or adjust the size of the lamina to the specific value, a known method may be adopted such as grinding the lamina obtained above by a dry ball mill, a wet ball mill, an oscillating mill, a roll mill or a Jet mill, or one or more classification methods selected from wet classification methods using oscillation screen such as gyroshifter or hammer screen; spiral classificator; and hydraulic power classificator, dry classification methods using dynamic or centrifugal air classificator and ore floatation methods (see, e.g. "Handbook of Particle Technology", edited by Kouichi Iitani, published by Asakura Shoten).

In general, the greater the difference in refractive index between the matrix and the finely divided metal or metal compound dispersed therein, the greater the UV screening ability due to the capacity of scattering ultraviolet rays. Therefore, the difference in refractive index between the matrix and the finely divided metal or metal compound dispersed therein is preferably 0.1 or more, more preferably 0.3 or more. When it is less than 0.1, the capacity of scattering ultraviolet rays and the UV screening ability tend to become insufficient.

For example, in the case where an organic compound of a high molecular weight or silica having a refractive index of 1.4–1.5 is used as the matrix, it is preferable to use alumina having a refractive index of 1.76 as the finely divided metal or metal compound, more preferably zinc oxide having a refractive index of 2.0 or titania having a refractive index of 2.5, whereby the capacity of scattering ultraviolet rays and UV screening ability are highly improved.

On the contrary, in the case where zinc oxide, titania or the like having a high refractive index is used as the matrix, it is preferable to use silica, alumina or the like having a low refractive index as the finely divided metal or metal compound.

A composite compound comprising one of the above-mentioned oxides, carbides or nitrides may be useful since the refractive index can be varied depending upon the mixing ratio. For example, a composite oxide consisting of silica and alumina at a weight ratio of 90:10 has a refractive index of about 1.7, whereas that at a weight ratio of 80:20 has a refractive index of about 1.65. A composite oxide consisting of titania and silica at a weight ratio of 50:50 has a refractive index of about 1.8, whereas that at a weight ratio of 25:75 has a refractive index of about 1.6.

The combination and proportion of the matrix and the finely divided metal or metal compound may be varied depending upon the size thereof or the purpose of use. For example, in the case of use as a UV screener where the transparency is important, it is preferable to disperse uniformly in a laminar substance having a low refractive index as a matrix a superfinely divided metal or metal compound having an average particle diameter of 0.1 $\mu$m or less and a high refractive index in an amount as small as possible. However, when the transparency is not important, the average particle diameter and proportion of the finely divided metal or metal compound are not so restrictive.

The laminar substance to be used as a matrix in the lamina of the present invention, and the finely divided metal or metal compound to be dispersed in the laminar substance are selected depending upon the purpose of use of the lamina: For example, where the heat resistance at a temperature of 200° C. or more is required, a metal oxide, a metal nitride, a metal carbide or an inorganic compound of a high molecular weight is suitable as the matrix. On the other hand, when the heat resistance at a temperature of not more than 100° C. is sufficient, conventional organic compounds of a high molecular weight is usable as the matrix and less expensive.

When the volume fraction of the finely divided metal or metal compound to be dispersed in the matrix exceeds 52%, the finely divided metal or metal compound serves as the matrix and the resulting lamina comes to have the properties of the finely divided metal or metal compound as a matrix. Therefore, if it is possible to form the matrix using the constituent of the finely divided metal or metal compound and form the finely divided particles using the constituent of the matrix, it may be, in some cases, easier to prepare a lamina by such a method.

However, generally, it is not always possible to exchange the constituent of the laminar substance and the finely divided particle. In view of ease of production, the volume fraction of the finely divided metal or metal compound is preferably about 0.1 to about 50%, more preferably about 1 to about 30% in view of practical use.

When the volume fraction of the finely divided metal or metal compound is too large, the properties of the resulting lamina becomes governed by the properties of the finely divided metal or metal compound, and hence, the combination effect becomes insignificant and the production of the lamina becomes difficult. On the contrary, when the volume fraction of the finely divided metal or metal compound is too small, the properties of the lamina tends to become substantially the same as those of the matrix, and the scattering of ultraviolet rays, for example, tends to be insufficient.

If a colored lamina is intended, colored finely divided metal or metal compound and/or colored laminar substance may be used. Especially, colored finely divided metal or metal compound should be used. For example, when red pigment such as iron oxide or the like is used, the lamina can be reded, when Green No. 2, chromium oxide or the like is used, the lamina can be greened and when molybdenum oxide or the like is used, the lamina can be blued.

The lamina thus obtained can be contained in various make-up and basic cosmetics such as day cream, powder foundation, face powder, lip stick, eye shadow and the like comprising UV screener so as to screen skin from harmful ultraviolet rays.

The content of the lamina of the present invention in the cosmetics can be varied depending upon the type of the cosmetic. However, it is, in general, preferably about 0.5 to about 70% by weight, more preferably about 2 to about 40% by weight, based on the total weight of the cosmetic. When the content of the lamina is less than 0.5% by weight, the cosmetic tends to become low in capacity of screening ultraviolet rays. On the other hand, when the content exceeds 70% by weight, the feel in use of the cosmetic such as soft and moist touch or the like becomes unsatisfactory.

In order to improve the capacity of screening ultraviolet rays, known UV screeners may be used, such as derivatives of salycilic acid, benzoic acid, cinnamic acid and benzophenone; titania; zinc oxide; calcium carbide and the like, together with the lamina of the present invention.

Before blending the lamina of the present invention with the cosmetic, the lamina can be subjected to a surface treatment such as a surface coating treatment with conventional fats and oils, a treatment with surface active agents or a treatment with a metal soap such as zinc stearate or the like, which is usually used for the purpose of enhancing the dispersibility and service characteristics.

The lamina of the present invention can be blended with cosmetics by a known blending method such as by means of a Henschel mixer, a ribbon mixer, a twin-cylinder mixer or the like.

The following Examples and Comparative Examples further illustrate the present invention but should not be interpreted to limit the scope of the present invention.

EXAMPLES 1 TO 3 AND COMPARATIVE EXAMPLES 1 AND 2

1.9 g (0.1 mole) of $TiCl_4$ was reacted with 6.4 g (0.2 mole) of methanol. Then, 42 g of water was added thereto. The resulting solution was ultrasonically mixed with superfinely divided silica (mfd. by Nippon Aerosil Co., Ltd.) having an average particle diameter of 0.012 $\mu$m in an amount as shown in Table 1.

A clean slide glass was dipped into the mixture, then pulled up therefrom at a rate of 75 cm/min., and thereafter dried at 120° C. for 30 minutes in an air bath to obtain a lamina.

The resulting lamina was calcined first at 300° C. for 5 hours and subsequently at 700° C. for 2 hours to obtain a lamina consisting of laminar titania and finely divided silica dispersed therein which lamina had an average size of 7 $\mu$m and an average thickness of 0.8 $\mu$m.

Then, spectral transmittance of the lamina was measured. The results are shown in FIG. 1.

Figure 1:
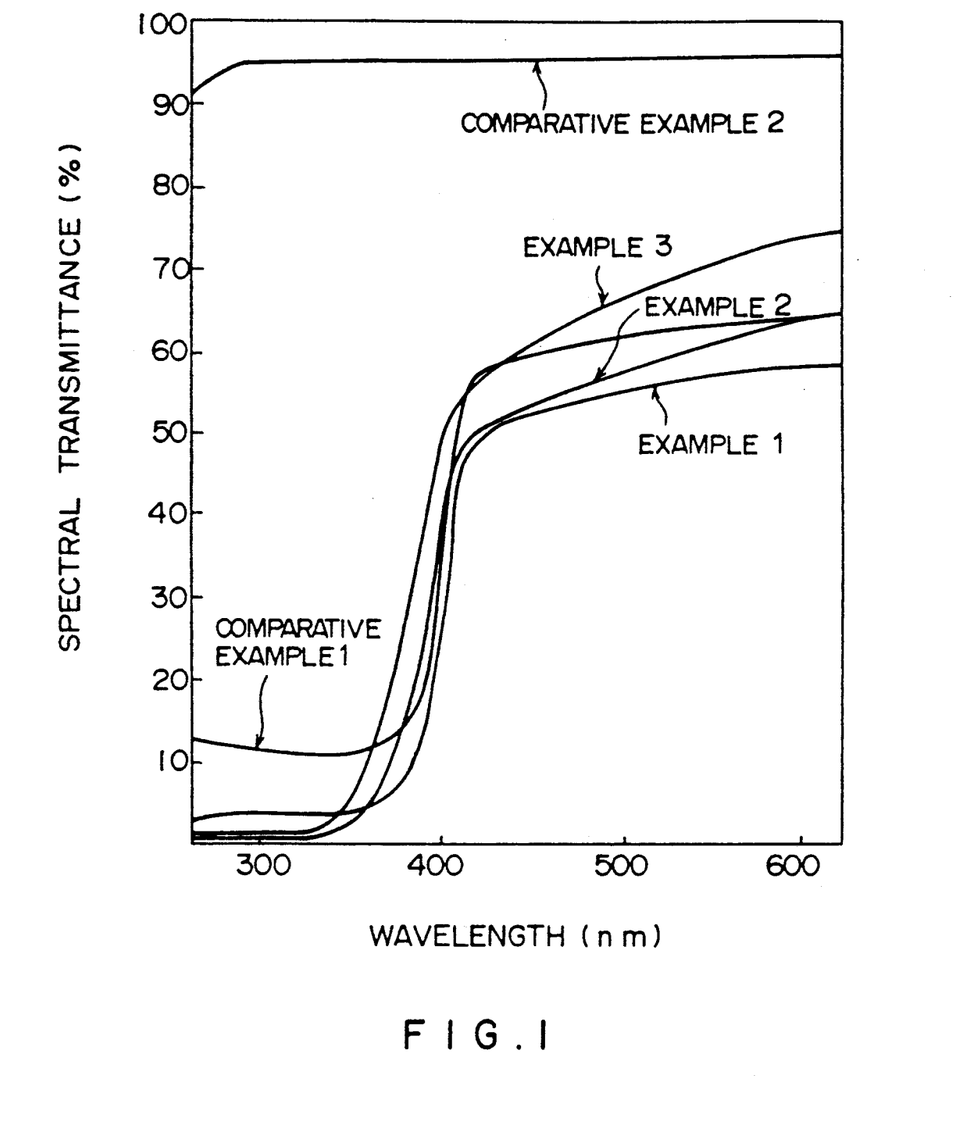
FIGS. 1, 2 and 3 are graphs showing spectral transmittances of the laminae of the present invention and commercially available, finely divided metal oxides at a wavelength ranging from 300 to 600 nm.

Also, spectral transmittance was measured on the lamina of Comparative Example 1 comprising laminar titania alone and the lamina of Comparative Example 2 comprising superfinely divided silica alone, and the results are also shown in FIG. 1.

The measurement of spectral transmittance was carried out as follows:

0.03 g of sample powder of the lamina was mixed with 0.47 g of low-density polyethylene powder and the resulting mixture was subjected to melt-kneading by means of a twin roll mill (temperature: 100°–160° C.) to obtain a film having a thickness of about 50 $\mu$m. A film of low-density polyethylene free of the sample powder which film had a thickness of about 50 $\mu$m was also prepared as control film in the same manner as above. Using this film as a control, spectral transmittance was measured on the sample film by a spectrophotometer in accordance with JIS K0115.

In these Examples and Comparative Examples, the refractive indexes of the finely divided silica and laminar titania were 1.46 and 2.5 respectively and the difference therebetween was 1.04.

COMPARATIVE EXAMPLES 3 TO 5

Spectral transmittance were measured on the rutile titania having an average particle diameter of 0.4 $\mu$m (mfd. by Ishihara Sangyo Kaisha Ltd.), the anatase titania having an average particle diameter of 0.3 $\mu$m (mfd. by Sakai Chemical Industry Co., Ltd.) and the finely divided titania having an average particle diameter of 0.03 $\mu$m (Nippon Aerosil Co., Ltd.).

Figure 2:
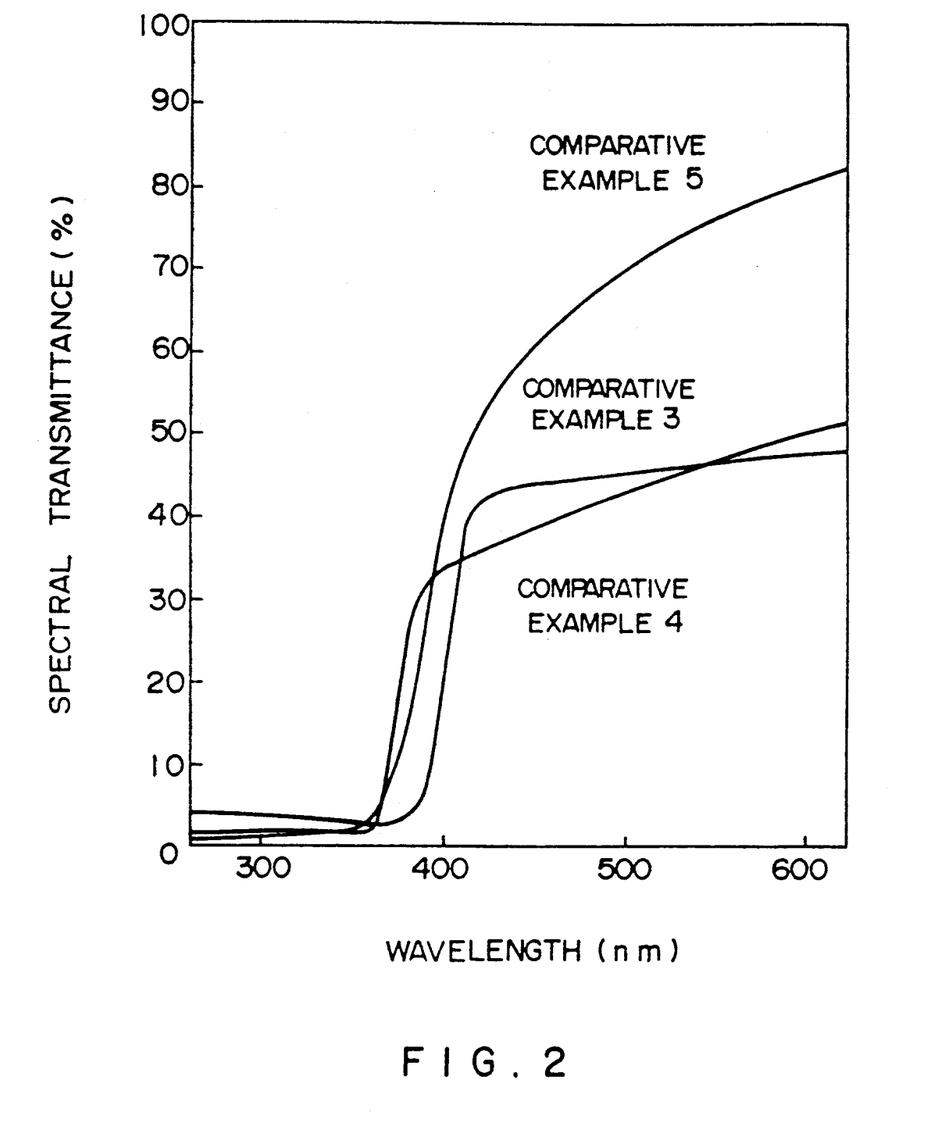

The results are shown in FIG. 2 as Comparative Examples 3 to 5 respectively.

EXAMPLE 4 AND COMPARATIVE EXAMPLE 6

To a 40% by weight ethanol solution of tetraethyl orthosilicate was added formic acid in an amount of two moles per mole of silicon contained in said solution. Then, the mixture was stirred at 70° C. for 3 hours. Thereafter, Superfinely divided titania having an average particle diameter of 0.03 μm (mfd. by Nippon Aerosil Co., Ltd.) was mixed ultrasonically therewith so that the amount of said titania was 30% by weight based on the weight of the silica contained in the mixture.

Next, a clean slide glass was dipped into the mixture. Then, it was pulled up therefrom in a rate of 75 cm/min. This laminated slide glass was dried at 90° C. for 30 minutes in an air bath to obtain a transparent surface-smooth lamina having an average size of 100 μm and an average thickness of 1.7 μm. The resulting lamina was calcined at 450° C. for 30 minutes to obtain a lamina having an average size of 60 μm and an average thickness of 0.9 μm consisting of laminar silica and superfinely divided titania dispersed therein.

Thereafter, this lamina was subjected to an ultrasonic grinding to obtain a lamina having an average size of 35 μm and an average thickness of 0.9 μm consisting of laminar silica and superfinely divided ticania dispersed therein.

Figure 3:
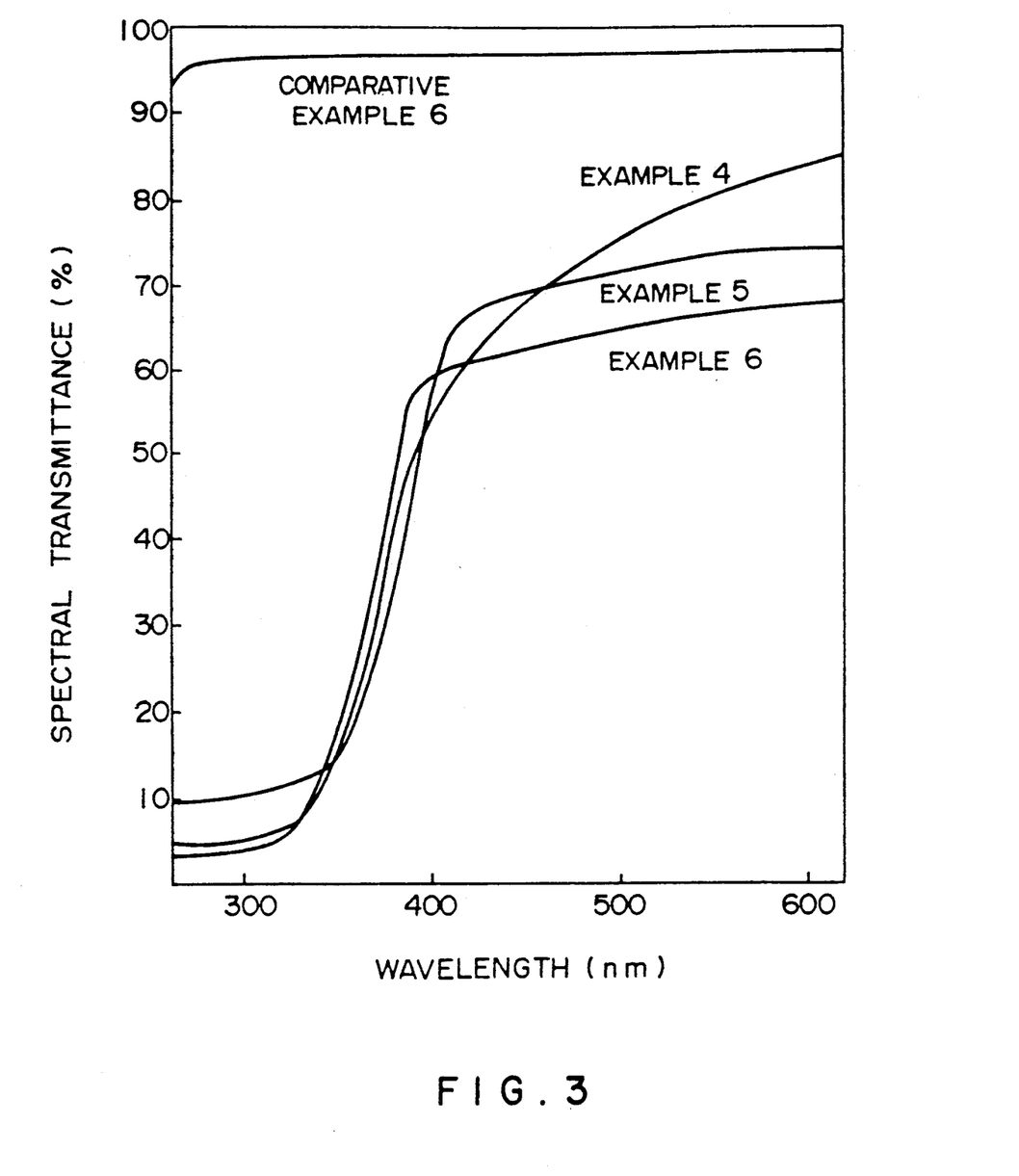

Spectral transmittance of the lamina was measured in the same manner as above. The result is shown in FIG. 3 as Example 4.

On the other hand, spectral transmittance of the lamina having an average size of 35 μm and an average thickness of 0.9 μm consisting of laminar silica alone was measured in the same manner as above. The result is also shown in FIG. 3 as Comparative Example 6.

In the Example, the refractive indexes of the superfinely divided titania and the laminar silica were 2.5 and 1.46 respectively and the difference therebetween was 1.04.

EXAMPLE 5

To 200 g of 40% by weight ethanol solution of titanium tetraethoxide were added 27 g of propionic acid and 1.4 g of finely divided alumina having an average particle diameter of 0.1 μm (mfd. by Sumitomo Chemical Co., Ltd.) in an amount of 5% by weight based on the calculated weight of titania. Then, the mixture was stirred at 70° C. for 3 hours. Thereafter, a clean slide glass was dipped into this mixture.

This slide glass was pulled up therefrom in a rate of 50 cm/min. and calcinated first at 90° C. for 30 minutes and subsequently at 450° C. for 30 minutes to obtain a lamina having an average size of 20 μm and an average thickness of 0.8 μm consisting of laminar titania and finely divided alumina dispersed therein.

Then the lamina was ground ultrasonically, and was subjected to levigation so that the average size becomes 10 μm.

Spectral transmittance of the resulting lamina was measured in the same manner as above. The result is shown in FIG. 3.

On the other hand, spectral transmittance of a lamina consisting of the finely divided titania obtained in the same manner as above was measured in the same manner as in Comparative Example 1.

In this Example, the refractive index of the finely divided alumina and laminar titania were 1.76 and 2.5 respectively and the difference therebetween was 0.74.

EXAMPLE 6 AND COMPARATIVE EXAMPLE 7

To a 30% by weight toluene solution of liquid epoxy resin was added finely divided zinc oxide having an average particle diameter of 0.05 μm in an amount of 40% by weight based on the weight of epoxy resin and mixed ultrasonically. Then, a clean slide glass was dipped into the resulting mixture.

The slide glass was pulled up therefrom in a rate of 50 cm/min. After drying at 100° C. for one minute, a lamina was obtained by scraping the lamina layer from the slide glass by a scraper. Then, the scraped lamina was dried at 100° C. for 10 minutes in an air bath.

The resulting lamina consisting of laminar epoxy resin and finely divided zinc oxide dispersed therein had an average size of 80 μm and an average thickness of 4 μm.

Spectral transmittance of the lamina was measured in the same manner as above. The result thereof is shown in FIG. 3 as Example 6.

On the other hand, a lamina consisting of laminar epoxy resin alone was obtained in the same manner as above. Spectral transmittances thereof at 300 and 500 nm are shown in Table 2 as Comparative Example 7.

EXAMPLE 7 AND COMPARATIVE EXAMPLE 8

With a 1% by weight tetrahydrofuran solution of polymethyl methacrylate was ultrasonically mixed finely divided zinc oxide having an average particle diameter of 0.05 μm in an amount of 50% by weight based on the weight of polymethyl methacrylate. This solution was coated on a stainless roll having a diameter of 10 cm rotating at 3 revolutions per minute at 60° C., and scraped the lamina layer therefrom by a scraper to obtain a lamina. The lamina obtained had a size distribution ranging from 20 to 200 μm and a thickness distribution ranging from 2 to 5 μm.

Then, the lamina having a size ranging from 10 to 70 μm was separated from the others by means of zigzag classificator. This separated lamina had a thickness distribution ranging from 2 to 4 μm.

Spectral transmittances of the lamina consisting of laminar polymethyl methacrylate having dispersed therein finely divided zinc oxide were measured at 300 and 500 nm and the results are shown in Table 2 as Example 7.

On the other hand, spectral transmittances of a lamina consisting of laminar polymethyl methacrylate alone were also measured and are shown in Table 2 as Comparative Example 8.

EXAMPLE 8 AND COMPARATIVE EXAMPLE 9

With an aluminum primary phosphate solution having a phosphorous content of 7% by weight and a molar ratio of aluminum to phosphorous of 3/1 were ultrasonically mixed finely divided titania having an average particle diameter of 0.03 μm in an amount of 5% by weight based on the weight of aluminum phosphate.

Then, a clean slide glass was dipped into this solution. Thereafter, it was pulled up therefrom in a rate of 50 cm/min. and dried at 90° C. for 30 minutes in an air bath. Then, a lamina was obtained by scraping the lamina layer from the slide glass by a scraper.

The lamina obtained consisting of laminar aluminum phosphate and finely divided titania dispersed therein had an average size of 20 μm and an average thickness of 2 μm.

Spectral transmittances of lamina were measured at 300 and 500 nm. The results are shown in Table 2 as Example 8.

On the other hand, spectral transmittances of a lamina consisting of laminar aluminum phosphate alone obtained in the same manner as above were measured at 300 and 500 nm. The results are shown in Table 2 as Comparative Example 10.

EXAMPLE 9

To 200 g of 40% by weight ethanol solution of titanium tetraethoxide were added 27 g of propionic acid and 2.8 g of zinc oxide having an average particle diameter of 0.03 μm. Then, the mixture was stirred at 70° C. for 3 hours. A clean slide glass was dipped into the mixture.

This slide glass was pulled up therefrom at a rate of 50 cm/min. and was dried at 90° C. for 30 minutes and calcinated at 450° C. for 30 minutes in an air bath to obtain a lamina having an average size of 15 μm and an average thickness of 0.8 μm consisting of laminar titania and finely divided zinc oxide dispersed therein. Then, this lamina was subjected to ultrasonic grinding and levigation to obtain a lamina having an average size of 10 μm.

Spectral transmittances of the resulting lamina were measured at 300 and 500 nm and the results are shown in Table 2.

EXAMPLE 10 AND COMPARATIVE EXAMPLES 10 AND 11

To 200 g of 40% by weight ethanol solution of titanium tetraethoxide was added 27 g of propionic acid. On the other hand, to 40% by weight ethanol solution of tetraethyl orthosilicate was added formic acid in an amount of two moles per mole of silicon contained in said solution. Then, both the solution were mixed together so that the volume ratio of $TiO_2/SiO_2$ was 75/25 (Example 10) or 50/50 (Comparative Examples 10 and 11). Thereafter, the mixtures were stirred at 70° C. for 3 hours and then ultrasonically mixed with 1.4 g of alumina having an average particle diameter of 0.1 μm (mfd. by Sumitomo Chemical Co., Ltd.) in the amount shown in Table 2.

Then, a clean slide glass was dipped into each mixture. After pulling up the slide glass therefrom at a rate of 75 cm/min., it was dried in an air bath at 90° C. for 30 minutes to obtain a transparent surface-smooth lamina having an average size of 100 μm and an average thickness of 1.7 μm.

Each lamina was calcined at 450° C. for 30 minutes to obtain a lamina having an average size of 60 μm and an average thickness of 0.9 μm comprising laminar titania-silica and finely divided titania dispersed therein.

Then, the lamina was further subjected to ultrasonic grinding to obtain a lamina having an average size of 10 μm and an average thickness of 0.9 μm comprising laminar titania-silica and finely divided titania dispersed therein.

Spectral transmittances of these resulting laminae were measured at 300 and 500 nm and the results thereof are shown in Table 2.

EXAMPLE 11 AND COMPARATIVE EXAMPLES 12 TO 14

Using the lamina consisting laminar titania and finely divided silica dispersed therein prepared in Example 2, a powder foundation was prepared.

For the comparison, powder foundation were prepared using the laminar titania of Comparative Example 1, commercially available powdery rutile titania having an average particle diameter of 0.4 μm (mfd. by Ishihara Sangyo Kaisha Ltd.) or a commercially available finely divided titania having an average particle diameter of 0.03 μm (Nippon Aerosil Co., Ltd.).

The method for preparing the powder foundations were as follows:

Powders such as titania, talc, sericite, yellow iron oxide, iron oxide red and the like were mixed together by a ribbon blender for 30 minutes. Then, with the resulting mixture was mixed liquid parafin, lanolin, squalane and the like by a Henschel mixer for 6 minutes. After perfumes were added thereto and mixed therewith for 2 minutes, the mixture obtained were subjected to screening and dieing to obtain a powder foundation.

Stability, UV screening ability and organoleptic properties were examined on the powder foundations of Example 10 and Comparative Examples 12 to 14. The results are shown in Table 3.

EXAMPLE 12 AND COMPARATIVE EXAMPLE 15

Using the lamina of Example 2 consisting of laminar titania and finely divided silica dispersed therein, a pressed powder was prepared.

On the other hand, for the comparison, a pressed powder mainly composed of talc was prepared.

Method for preparing the pressed powders was as follows:

Pigments were blended by a blender. Thereto were added the rest of the materials. Then, the blend was colored, sprayed with perfumes and further mixed together. Thereafter, the resulting mixture was subjected to press molding to obtain a pressed powder.

Stability, UV screening ability and organoleptic properties were examined on the pressed powder of Example 12 and Comparative Example 15. The results are shown in Table 4.

The methods for examining the stability, UV screening ability and organoleptic properties were as follows:

Stability

Changes of properties of the cosmetics were examined after one year-storage in a room without temperature control.

UV Screening Ability (SPF Value, Suntan Preventing Factor)

With ultraviolet rays were irradiated a skin portion with a uniform cosmetic coating of 2 mg/cm$^2$ or 2 μl/cm$^2$ or a skin portion without cosmetic coating by a medical UV irradiator manufactured by The Toko Electric Corp. [M-DMR-1, illuminant: Toshiba Fluorescent Lightings: FL20S·E-30 ($\lambda_{max}$: 305 nm) and FL20S·BLB ($\lambda_{max}$: 352 nm)]. Minimum energy for forming red spots were measured by an ultraviolet dosimeter mfd. by Tokyo Optical Co., Ltd. (UVR-305/365 D) on each case. The screening ability is indicated by a ratio of minimum energy for forming red spots on the skin portion with the cosmetic coating to minimum energy for forming red spots on the skin portion without cosmetic coating.

Organoleptic Properties

Cosmetics were used by 20 women for two weeks. Thereafter, the cosmetics were evaluated by them on every item in 5 ratings, in which 5 indicated the best and 1 indicated the worst. The results shown in Tables 3 and 4 are mean values thereof.

TABLE 1

| | Amount of Laminar Titania (parts by weight) | Amount of Finely-Divided Silica (parts by weight) | Spectral Transmittance at 300 nm (%) |
|---|---|---|---|
| Example 1 | 97 | 3 | 3 |
| Example 2 | 85 | 15 | 1 |
| Example 3 | 70 | 30 | 1.5 |
| Comparative Example 1 | 100 | 0 | 12 |
| Comparative Example 2 | 0 | 100 | 95 |

TABLE 2

| | Matrix | | Dispersed Particle | | | | Spectral Transmittance (%) | |
|---|---|---|---|---|---|---|---|---|
| | Substance | Refractive Index | Substance | Average Size (μm) | Mixed Amount (% by weight) | Refractive Index | Ultraviolet (300 nm) | Visible (500 nm) |
| Example 6 | Epoxy Resin | 1.5 | ZnO | 0.03 | 40 | 2.0 | 3 | 65 |
| Comparative Example 7 | Epoxy Resin | 1.5 | — | — | — | — | 50 | 70 |
| Example 7 | PMMA | 1.5 | ZnS | 0.05 | 50 | 2.36 | 1.5 | 60 |
| Comparative Example 8 | PMMA | 1.5 | — | — | — | — | 95 | 95 |
| Example 8 | Aluminum Phosphate | 1.56 | TiO$_2$ | 0.03 | 5 | 2.5 | 15 | 75 |
| Comparative Example 9 | Aluminum Phosphate | 1.56 | — | — | — | — | 60 | 90 |
| Example 9 | TiO$_2$ | 2.5 | ZnO | 0.03 | 10 | 2.0 | 7.5 | 61 |
| Example 10 | TiO$_2$/SiO$_2$ | 2.0 | Al$_2$O$_3$ | 0.1 | 30 | 1.76 | 30 | 87 |
| Comparative Example 10 | TiO$_2$/SiO$_2$ | 1.8 | Al$_2$O$_3$ | 0.1 | 30 | 1.76 | 40 | 90 |
| Comparative Example 11 | TiO$_2$/SiO$_2$ | 1.8 | — | — | — | — | 45 | 90 |

TABLE 3

Powder Foundation

| Proportion (% by weight) | Example 3 | Comparative Example 10 | Comparative Example 11 | Comparative Example 12 |
|---|---|---|---|---|
| Laminar Titania Containing Finely Divided Particle | 55 | 0 | 0 | 0 |
| Laminar Titania | 0 | 55 | 0 | 0 |
| Powdery Titania | 0 | 0 | 30 | 0 |
| Finely Divided Titania | 0 | 0 | 0 | 20 |
| Talc | 0 | 0 | 25 | 30 |
| Sericite | 25 | 25 | 25 | 30 |
| Yellow Iron Oxide | 6 | 6 | 6 | 6 |
| Iron Oxide Red | 2 | 2 | 2 | 2 |
| Liquid Parafin | 2 | 2 | 2 | 2 |
| Lanoline | 4 | 4 | 4 | 4 |
| Squalane | 2 | 2 | 2 | 2 |
| Others | 4 | 4 | 4 | 4 |
| Perfumes | 0.2 | 0.2 | 0.2 | 0.2 |
| Organoleptic Examination | | | | |
| Spreading | 4.6 | 4.6 | 1.5 | 2.2 |
| Adhesiveness | 4.5 | 4.5 | 4.0 | 3.8 |
| Luster | 4.7 | 4.7 | 2.7 | 3.6 |
| Color Sense | 4.8 | 4.7 | 2.1 | 4.0 |
| Stability | No Change | No Change | No Change | Change |
| SPF Value | 10 | 5 | 8 | 10 |

TABLE 4

Pressed Powder

| Proportion (% by weight) | Example 12 | Comparative Example 15 |
|---|---|---|
| Iron Oxide Red | 0.4 | 0.4 |
| Yellow Iron Oxide | 0.2 | 0.2 |
| Black Iron Oxide | 0.1 | 0.1 |
| Sericite | 22.1 | 22.1 |
| Talc | 30.0 | 70.0 |
| Low-Luster Laminar Titania | 40.0 | 0.0 |
| Zinc Stearate | 3.0 | 3.0 |
| Squalane | 2.0 | 2.0 |
| Methylphenyl polysiloxane | 2.0 | 2.0 |
| Anti-Oxidant | trace | trace |
| Antiseptic | trace | trace |
| Perfumes | 0.2 | 0.2 |
| Organoleptic Examination | | |
| Spreading | 4.8 | 4.8 |
| Adhesiveness | 5.0 | 3.5 |
| Luster | 4.5 | 4.0 |
| Smoothness & Moist | 4.5 | 3.8 |
| Stability | No Change | No Change |
| SPF value | 8 | 1 |

What is claimed is:

1. A lamina having an excellent capacity to scatter ultraviolet rays comprising:

a laminar substance as a matrix and a finely divided metal or metal compound dispersed therein, wherein the difference in refractive index between the laminar substance and the finely divided metal or metal compound is not less than 0.1, the volume fraction of the finely divided metal or metal compound is 0.1-50%, the laminar substance has an average thickness of 0.1-5 μm and an average size of 1-500 μm, the laminar substance is at least one member selected from the group consisting of bivalent or higher polyvalent metals; oxides, nitrides, carbides and hydroxides of the metals; hydrolysates of metal chlorides; partial hydrolysates of organometallic compounds; and inorganic and organic compounds of a higher molecular weight, and the finely divided metal or metal compound is at least one member selected from the group consisting of bivalent or higher polyvalent metals; oxides, nitrides, carbides and hydroxides of the metals; hydrolysates of metal chorides; partial hydrolysates of organometallic compounds; and metal sulfates.

2. A lamina according to claim 1, wherein the difference in refractive index between the laminar substance and the finely divided metal or metal compound is not less than 0.3.

3. A lamina according to claim 1, wherein the volume fraction of the finely divided metal or metal compound is 1–30%.

4. A lamina according to claim 1, wherein the finely divided metal or metal compound has an average particle diameter of 0.008–0.1 μm.

5. A lamina according to claim 1, wherein the finely divided metal or metal compound is a metal oxide.

6. A lamina according to claim 5, wherein the metal oxide is titania, silica or zinc oxide.

7. A lamina according to claim 9, wherein the laminar substance has an average thickness of 0.2–2 μm.

8. A lamina according to claim 7, wherein the laminar substance has an average size of 3–100 μm.

9. A lamina according to claim 1, wherein the laminar substance is a metal oxide.

10. A lamina according to claim 9, wherein the metal oxide is titania or silica.

11. A lamina according to claim 1, wherein the laminar substance is an organic compound of a high molecular weight.

12. A lamina according to claim 11, wherein the organic compound is epoxy resin or polymethyl methacrylate.

13. A lamina according to claim 1, wherein the laminar substance is an inorganic compound of a high molecular weight.

14. A lamina according to claim 13, wherein the inorganic compound is aluminum phosphate.

15. A lamina according to claim 1, wherein the partial hydrolysates of organometallic compounds in the laminar substance and finely-divided metal or metal compound are at least one member selected from the group consisting of metal alkoxides, metal chelate compounds and metal salts of organic acids.

* * * * *